US006687536B1

(12) United States Patent
Beck et al.

(10) Patent No.: US 6,687,536 B1
(45) Date of Patent: Feb. 3, 2004

(54) CONNECTION SYSTEM FOR AN IONTOPHORETIC DRUG DELIVERY DEVICE

(75) Inventors: Jon E. Beck, Salt Lake City, UT (US); Brian Keith Leaf, Kearns, UT (US)

(73) Assignee: Iomed, Inc., Salt Lake City, UT (US)

( * ) Notice: Subject to any disclaimer, the term of this patent is extended or adjusted under 35 U.S.C. 154(b) by 0 days.

(21) Appl. No.: 09/458,239

(22) Filed: Dec. 9, 1999

(51) Int. Cl.[7] ............................................... A61N 1/30
(52) U.S. Cl. ...................... 604/20; 604/289; 604/890.1
(58) Field of Search ........................... 604/20, 19, 289, 604/290, 890.1; 607/152, 153

(56) References Cited

U.S. PATENT DOCUMENTS 5,284,471 A  *  2/1994  Sage, Jr. ........................ 604/20
5,562,607 A  * 10/1996  Gyory ........................... 604/20
5,603,693 A  *  2/1997  Frenkel et al. ................. 604/20
5,846,217 A  * 12/1998  Beck et al. .................... 604/20

* cited by examiner

Primary Examiner—Brian L. Casler
Assistant Examiner—Jeremy Thissell
(74) Attorney, Agent, or Firm—Factor & Partners

(57) ABSTRACT

A connection system for an iontophoretic drug delivery apparatus comprises an electrode assembly, a power source and a structure for facilitating mating engagement therebetween. The electrode assembly includes a first interface and two electrical leads and the power source includes a second interface and two electrical contacts. The interfaces are configured to facilitate mating engagement therebetween and operative secured electrical continuity between the electrical leads of the electrode assembly and the electrical contacts of the power source.

17 Claims, 4 Drawing Sheets

CONNECTION SYSTEM FOR AN IONTOPHORETIC DRUG DELIVERY DEVICE

BACKGROUND OF THE INVENTION

1. Field of the Invention

The present invention is directed to iontophoretic drug delivery systems, and more particularly to the interface structure between a power source and an electrode assembly.

2. Background Art

The use of iontophoretic drug delivery systems has been known in the art for several years. Such devices are generally used to deliver a drug to a patient through the patient's skin or through the patient's eye. Generally, such devices comprise an electrode assembly/patch and a power source/control module which is attached to the electrode assembly. Unfortunately, the attachment interface between the power source/control module and the electrode assembly suffers from some drawbacks.

Specifically, the interface structures commonly include an interface on both the electrode assembly and the power source, wherein one interface is matingly inserted into the other. Once mated, electrical contacts associated with the power source contact leads associated with the electrode assembly. Currently, because the interfaces engage in only one indexed position, the two interfaces must be substantially aligned before operative engagement therebetween. In addition, even when positioned in the proper indexed orientation, the actual "nested" engagement requires more effort than necessary.

Another problem with the prior art devices is that once the interface structures are mated, it can be difficult to maintain good electrical continuity between the contacts of the power source and the leads of the electrode assembly. While various complex structures have been proposed, it has been difficult to find a solution which requires few components, is cost effective and which is reliable for the user.

It is thus an object of the present invention to provide an interface structure which facilitates attachment between the power source and the electrode assembly of an iontophoretic drug delivery device.

It is likewise an object of the present invention to provide an interface structure which effectively maintains electrical continuity between the power source and the electrode assembly.

These and other objects of the present invention will become apparent in light of the present specification, drawings and claims appended hereto.

SUMMARY OF THE INVENTION

The present invention is directed to an iontophoretic drug delivery apparatus. The apparatus comprises an electrode assembly, a power source and means for facilitating mating engagement therebetween. The electrode assembly includes a first interface and two electrical leads and the power source includes a second interface and two electrical contacts. The facilitating means enables mating engagement of one of the first and second interfaces into the other of the first and second interfaces with limited need for pre-alignment therebetween. In turn, the two electrical leads of the electrode assembly are oriented into secured/locked abutment with the two electrical contacts of the power source.

In a preferred embodiment of the invention, the facilitating means comprises a tapering structure associated with the outer surface of one of the first and second interfaces, and, an outwardly expanding structure associated with the other of the first and second interfaces. The positioning of the tapering structure toward and into the outwardly expanding structure slidably enables mating engagement between the first interface and the second interface.

In such a preferred embodiment, the tapering structure and the outwardly expanding structure each comprise corresponding conical configurations. Such conical configurations can have either a uniform or non-uniform geometry.

In another preferred embodiment, the facilitating means may further include means for rotatively positioning one of the first and second interfaces into desired alignment with the other. For example, the desired alignment may be in at least any one of two predetermined angular orientations.

In a preferred embodiment, the rotative positioning means comprises both of the first and second interfaces having elongated, substantially eliptical cross-sections.

In yet another preferred embodiment, the apparatus includes means for retaining the first and second interface in a desired mated engagement. In one such preferred embodiment, the retaining means may comprise at least one detent associated with one of the first and second interface, and, at least one biased tab associated with the other of the first and second interface. The biased tab lockably cooperates with an associated detent upon positioning of the first and second interface into a mated orientation.

In still another preferred embodiment, the apparatus may include means for biasing the leads of the electrode assembly with the electrical contacts of the power supply upon mating engagement therebetween. In one such embodiment, the biasing means may comprise an elastically deformable material associated with the leads. The elastically deformable material is associated with the first interface such that, upon mating engagement of the first and second interface, the contacts of the second interface elastically deform the material, which, in turn, biases the leads into electrical connection with the contacts.

In yet another preferred embodiment, the apparatus may further include a seal member (such as an O-ring) associated with one or both of the first and second interfaces. The seal member seals the underside of the power source from undesired contamination, such as moisture.

The invention may further include means for electrically connecting the two electrical leads with the electrical contacts in any one of at least two orientations. Preferably, the orientations are achieved by rotating either the electrode assembly or the power source, relative to the other, about an axis. In turn, the electrical connecting means comprises the positioning of an electrical lead of the electrode assembly and one of the two electrical contacts of the power source about a common axis of rotation.

In such a preferred embodiment, a second electrical contact is spaced apart from the axis of rotation a predetermined distance, and a second electrical lead is likewise positioned a predetermined distance apart from the axis of rotation. The second electrical lead is positioned so that the second electrical contact engages the second electrical lead in any of the at least two orientations.

In another preferred embodiment, the first orientation and the second orientation are separated by an angular distance of about 180 degrees.

BRIEF DESCRIPTION OF THE DRAWINGS

The invention will now be described with reference to the drawings wherein.

BEST MODE FOR PRACTICING THE INVENTION

Figure 1A:
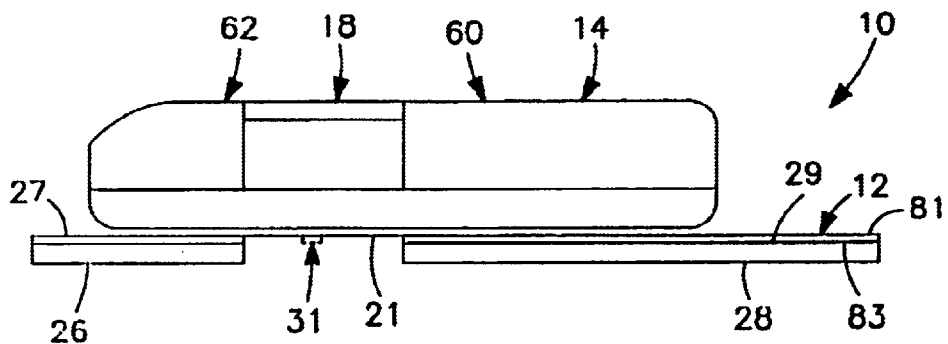
FIG. 1a of the drawings is a side elevational view of the power source and the electrode assembly in a first orientation.

While this invention is susceptible of embodiment in many different forms, there is shown in the drawings and will be described in detail, several specific embodiments with the understanding that the present disclosure is to be considered as an exemplification of the principles of the invention and is not intended to limit the invention to the embodiments illustrated.

Iontophoretic drug delivery apparatus 10 is shown in FIG. 1a as comprising electrode assembly 12, power source 14 (which may comprise a dose controller with conventional electronic circuitry), means 16 (FIGS. 3 and 4) for facilitating mating engagement of the electrode assembly and the power source, means 18 for retaining such mating engagement, means 20 (FIG. 7) for electrically connecting the power source and the electrode assembly in at least two orientations, and, means 19 (FIG. 10) for biasing the electrical contacts of the power source with the electrical leads of the electrode assembly. As will be understood, the iontophoretic drug delivery system utilizes a power source to drive a medicament or other beneficial agent to a patient through the patient's tissue (for example, through a patient's skin or ocular region).

Figure 8:
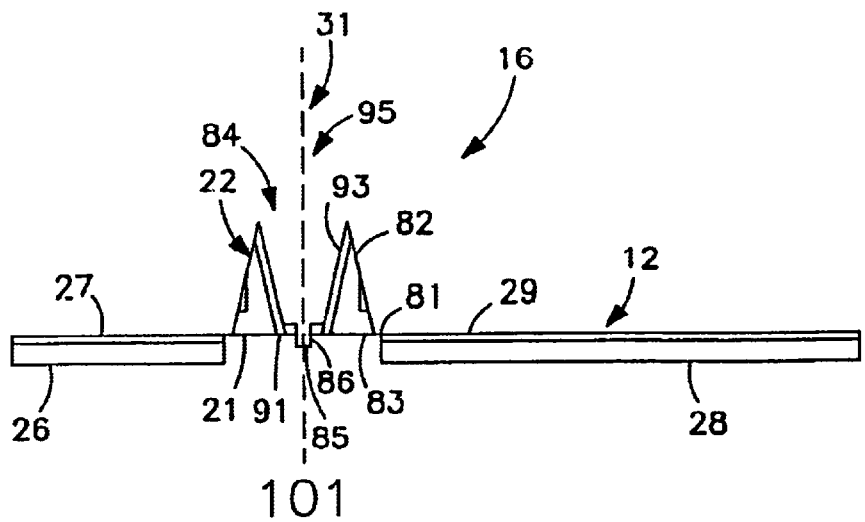
FIG. 8 of the drawings is a cross-sectional view of the electrode assembly taken about lines 8—8 of FIG. 2.
Figure 2:
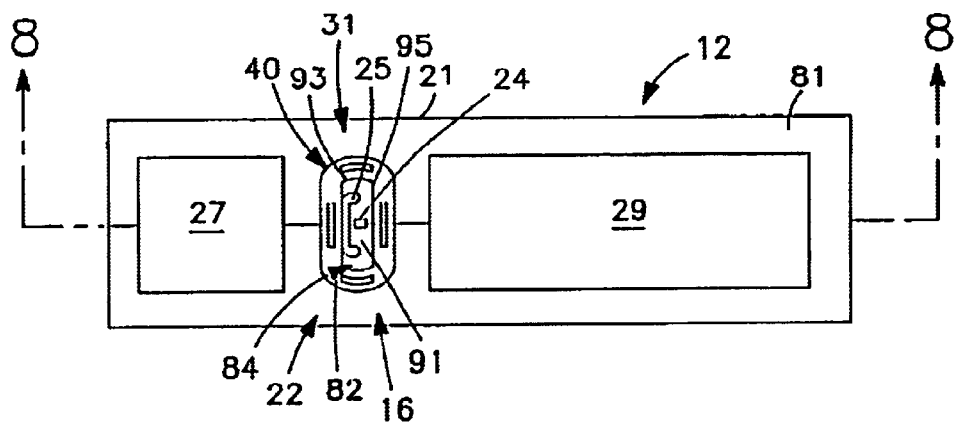
FIG. 2 of the drawings is a top plan view of the electrode assembly.
Figure 7:
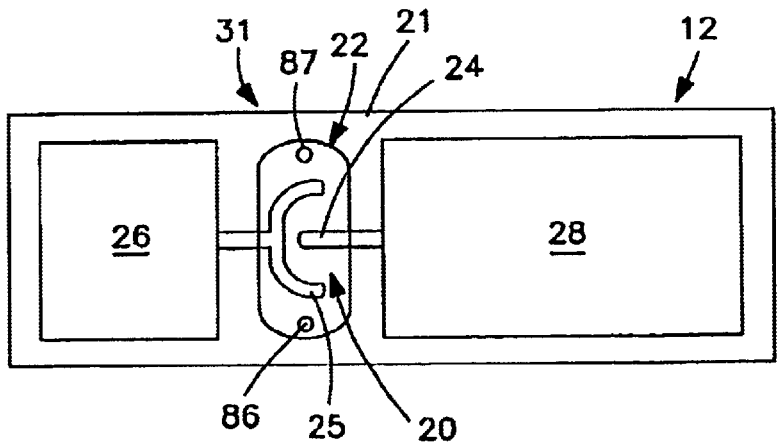
FIG. 7 of the drawings is a top plan view of the electrode assembly.
Figure 9:
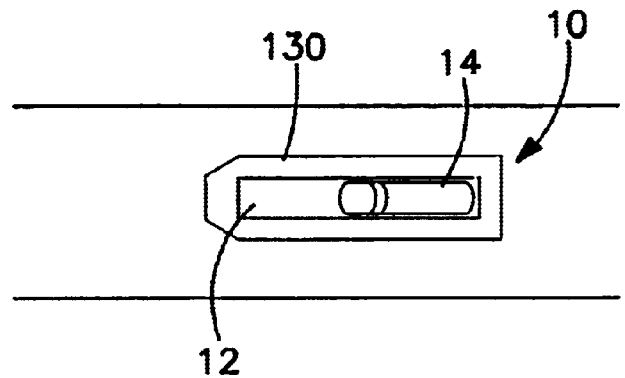
FIG. 9 of the drawings is a partial cross-sectional view of the apparatus taken generally about lines 10—10 of FIG. 1b.

Electrode assembly 12 is shown in detail in FIGS. 2, 7 and 8 as comprising base 21, first interface 22 (FIG. 8), leads 24, 25 (FIGS. 2 and 7), electrodes 27, 29 and electrode pads 26, 28. Base 21 includes upper surface 81, lower surface 83 and central region 31. The base comprises a substantially liquid impervious planar material, such as, for example, mylar or the like. Pads 26, 28 are positioned on the lower surface of base 21, and comprise a material which is capable of absorbing and controllably releasing a fluid (i.e. medicament or beneficial agent) through iontophoresis. While differently dimensioned pads are shown in FIG. 2, it will be understood that the particular dimensions are not limited and may be sized differently for different applications.

Electrodes 27, 29 are positioned between pads 26, 28 and base 21, so as to be in abutting contact with the pads. Leads 24 and 25 extend from the electrodes on the lower surface of base 21 to central region 31 of the upper surface of the base. The electrodes and the leads may comprise a variety of conventional materials, such as aluminum, silver, copper and the like. In addition, in one preferred embodiment, the leads can be printed (through conventionally known techniques) onto the surface of the elastically deformable material/base of the electrode assembly.

Figure 3:
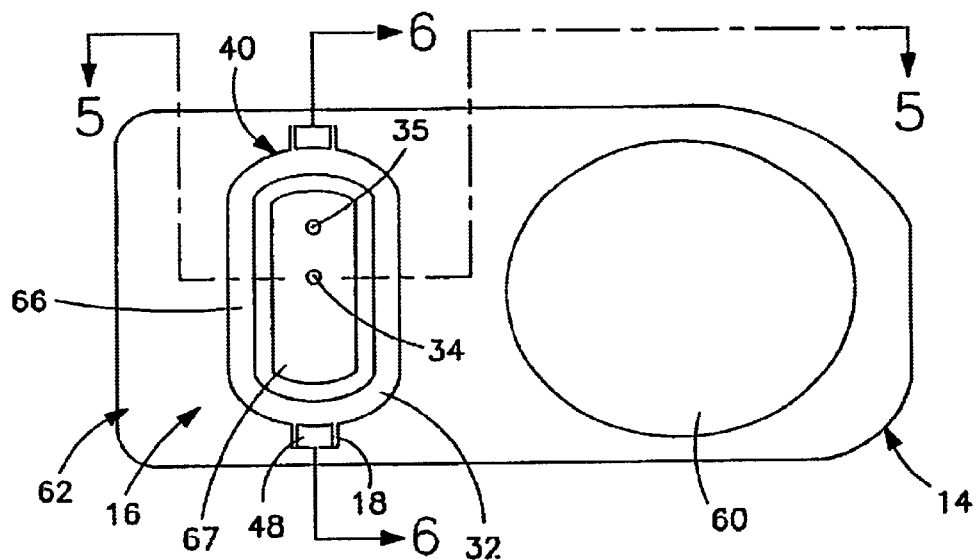
FIG. 3 of the drawings is a bottom plan view of the power source.
Figure 4:
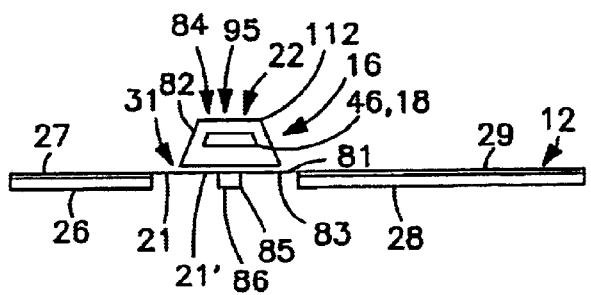
FIG. 4 of the drawings is a side elevational view of the electrode assembly.

Mating engagement means 16 (FIG. 4) includes first interface 22 and second interface 32 (FIG. 3). First interface 22 is shown in FIGS. 4 and 8 as comprising outer surface 82, inner region 84 and attachment means 85. Inner region 84 includes lower surface 91 (FIG. 8) and side surface 93. As will be explained below, the configuration of outer surface 82 facilitates mating engagement of electrode assembly 12 and power source 14.

As can be seen in FIGS. 2 and 8, first interface 22 is attached by way of attachment means 85 to central region 31 of base 21 so that leads 24 are proximate lower surface 91 of inner region 84. Specifically, attachment means 85 comprises pegs 86, 87 (FIG. 7) which are inserted through corresponding openings in base 21 and subsequently deformed (such as by swaging) to secure first interface 22 to base 21. The pegs are preferably fabricated from a non-conductive material, such as plastic. Although, pegs have been disclosed, other types of attachment means are likewise contemplated, such as attachment through thermal welding or adhesives.

Second interface 32, is shown in FIGS. 1a and 3 as being integrated with power source 14. The power source comprises power supply 60, dose control means 62, and electrical contacts 34, 35 (FIG. 3). In a preferred embodiment, power supply 60 includes a battery suitable of providing the necessary power to the apparatus. Various batteries are suitable for use, including both primary and secondary batteries (i.e. NiMH, NiCd, Li-ion and alkaline, etc.). Dose control means 62 may comprise conventional analog and/or digital circuitry which can monitor the application of power to electrical contacts 34, 35. Various dose control means can be utilized, and the invention is not limited to any particular dose control means. In addition, while a portable battery operated power source is shown, the invention is equally applicable to AC/DC operated hand held units which are stand alone structures separate from the electrode assembly.

Figure 5:
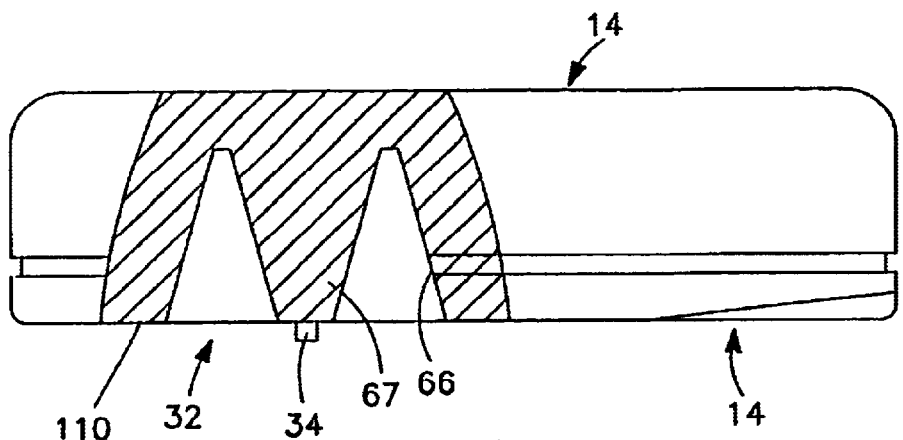
FIG. 5 of the drawings is partial cross-sectional view of the power source taken generally about lines 5—5 of FIG. 3.
Figure 6:
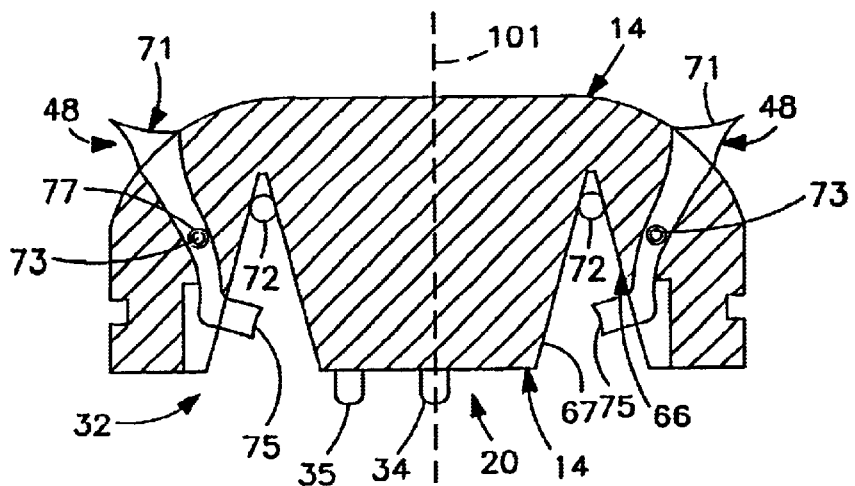
FIG. 6 of the drawings is a partial cross-sectional view of the power source taken generally about lines 6—6 of FIG. 3.

Second interface 32 is shown in detail in FIGS. 3, 5 and 6 as comprising inner surface 66, projecting member 67 and sealing member 72. As will be explained, inner surface 66 is configured so as to cooperate with outer surface 82 of first interface 22 so as to direct the first and second interfaces into mating engagement therebetween. Projecting member 67 is configured to matingly nest within inner region 84 of first interface 22. Electrical contacts 34, 35 are disposed on projecting member 67 so as to electrically abut with leads 24, 25 of electrode assembly 12 once the first and second interfaces are mated. In addition to the above, the projecting member also facilitates alignment between the interfaces by operatively guiding the interfaces into mating engagement with each other.

Seal member 72 is shown in FIG. 6 as comprising an O-ring or other flexible elastomeric member positioned in the base of the slot defined by projecting member 67 and inner surface 66. The seal member substantially precludes the passage of contamination and moisture into the interior of the power source during and after mating of the two interfaces. While the seal member is shown as being associated with the second interface, it is also contemplated that it be associated with lower surface 91 of first interface 22. It is also contemplated that additional seals or other structures which protect the contacts and leads from moisture and contamination may also be utilized.

While the first interface is shown as being associated with electrode assembly 12, and, the second interface is shown as being associated with power source 14, it will be understood that first interface may be associated with power source 14 and that second interface may be associated with electrode assembly 12.

First interface 22 is shown in FIG. 4 as comprising outer surface 82 having a tapered configuration. For example, the outer surface tapers from the bottom up into a conical geometry. In turn, inner surface 66 (FIG. 5) of second interface 32 has a geometry which enables slidable and matable cooperation within the first interface. By configuring outer surface 82 of the first interface, and inner surface 66 of the second interface, as mentioned, aligned attachment therebetween is facilitated. Indeed, as the respective surfaces are placed into abutment and as the user forces the interfaces together, the abutting surfaces will naturally direct the first and second interfaces into an operative fully engaged orientation.

To further facilitate engagement, it is also contemplated that the slope of surfaces 82 (FIG. 4) and 66 (FIG. 5) may be non-uniform. Specifically, decreasing the slope of these surfaces at regions 110 (FIG. 5) and 112 (FIG. 4), respectively, further facilitates the mating engagement between the first and second interfaces.

Rotative positioning means 40 is collectively shown in FIGS. 2 and 3 as comprising outer surface 82 of first interface 22 and inner surface 66 of second interface 32 each having elongated elliptical cross-sections. As such, as long as the user can initiate contact of outer surface 82 with inner surface 66, the first and second interfaces will be engageably rotated relative to each other until they are positioned into their fully engaged orientation. Furthermore, as exemplified in FIGS. 1a and 1b, aligned attachment of the power source with the electrode assembly can be achieved in either of two orientations, specifically, substantially 180 degrees apart. While the inner and outer surfaces of the first and second interfaces, respectively, have been shown and described as elongated and elliptical other geometries are also contemplated, provided they facilitate operative rotation in a manner similar to that as described.

Retaining engagement means 18 is shown in FIG. 3 and FIG. 4 as comprising biased tabs 48 (FIG. 3 and FIG. 6), and detents 46 (FIG. 4). As can be seen, detents 46 are formed into outer surface 82 of first interface 22, and each of the biased tabs 48 are associated with second interface 32. As shown in FIG. 6, each of the biased tabs include handle member 71, pivot axis 73, engagement region 75 and biasing spring 77. Upon operative engagement between the first and second interfaces, engagement region 75 of tab 48 lockably extends into detent 46 of first interface 32, to, in turn, releasably lock the first and second interfaces together. Such a releasably lockable orientation is maintained as a result of biasing spring 77. Although the biasing spring preferably comprises a coil spring, other conventional biasing elements are also contemplated for use.

Electrical connecting means 20 is shown in FIGS. 6 and 7 as comprising the spacial positioning of first and second leads 24, 25, respectively of electrode assembly 12, and first and second contacts 34, 35, respectively, of power source 14.

Figure 1B:
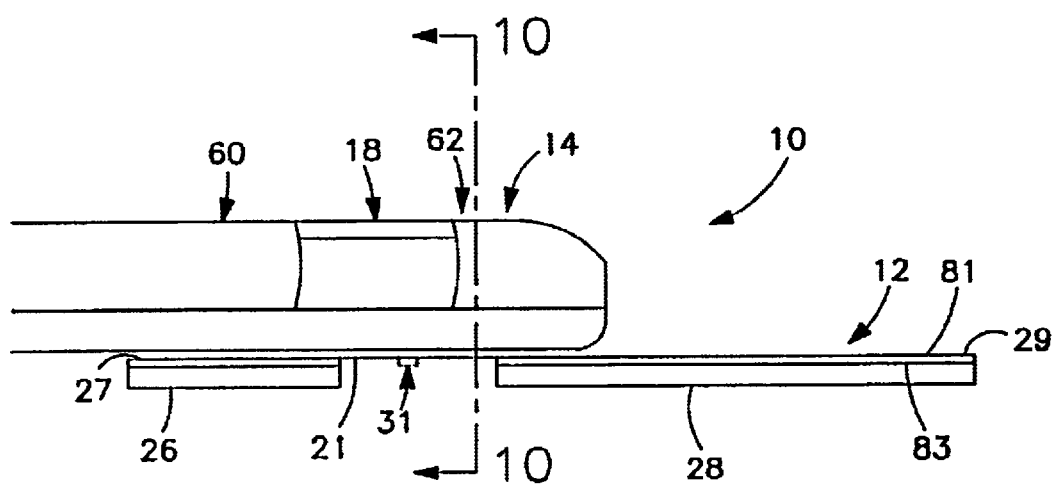
FIG. 1b of the drawings is a side elevational view of the power source and the electrode assembly in a second orientation.

Such spacial positioning enables electrical connection to be established in at least two orientations. In particular, to facilitate electrical connection, first contact 34 and first lead 24 are both positioned about the axis of rotation 101 (FIG. 6 and FIG. 8) of first interface 22 relative to the second interface 32. As shown in FIG. 6, second contact 35 is spaced apart from first contact 34 a predetermined distance. Likewise, a portion of second lead 25 is positioned on either side of first lead 24 and spaced apart a distance corresponding to the distance separating first and second contacts 34, 35, respectively. As such, whether the electrode assembly and the power source are joined in a first orientation, as shown in FIG. 1a, or, when either the electrode assembly or the power source are rotated 180 degrees into a second orientation, as shown in FIG. 1b, first contact 34 will always be electrically connected with first lead 24, and second contact 35 will always be electrically connected to one of the two portions of second lead 25.

It will be understood that depending on the shape of inner surface 66 of second interface 32 and outer surface 82 of first interface 22, the electrode assembly and the power source may be attachable in more than two orientations. For example, the electrode assembly and the power source can be capable of three mating orientations if first lead 24 (on the electrode assembly) and first contact 34 (on the power supply) are positioned about the axis of rotation 101 of the electrode assembly relative to the power source, and, provided that second lead 25 (on the electrode assembly) comprises three separate lead portions which are positioned radially and substantially equidistant from the first lead. As another example, one of the leads can comprise a circular configuration, and another lead can be positioned in the center of the circle about the axis of rotation of the associated power source. As still another example, it is contemplated that the leads comprise two concentric circles. In either of these last two embodiments, the power source can be operatively oriented into an infinite number of rotative positions. As will be readily understood to those having ordinary skill in the art, other geometries of the leads and interfaces, as well as the number of leads and contacts, are contemplated by the present invention.

Figure 10:
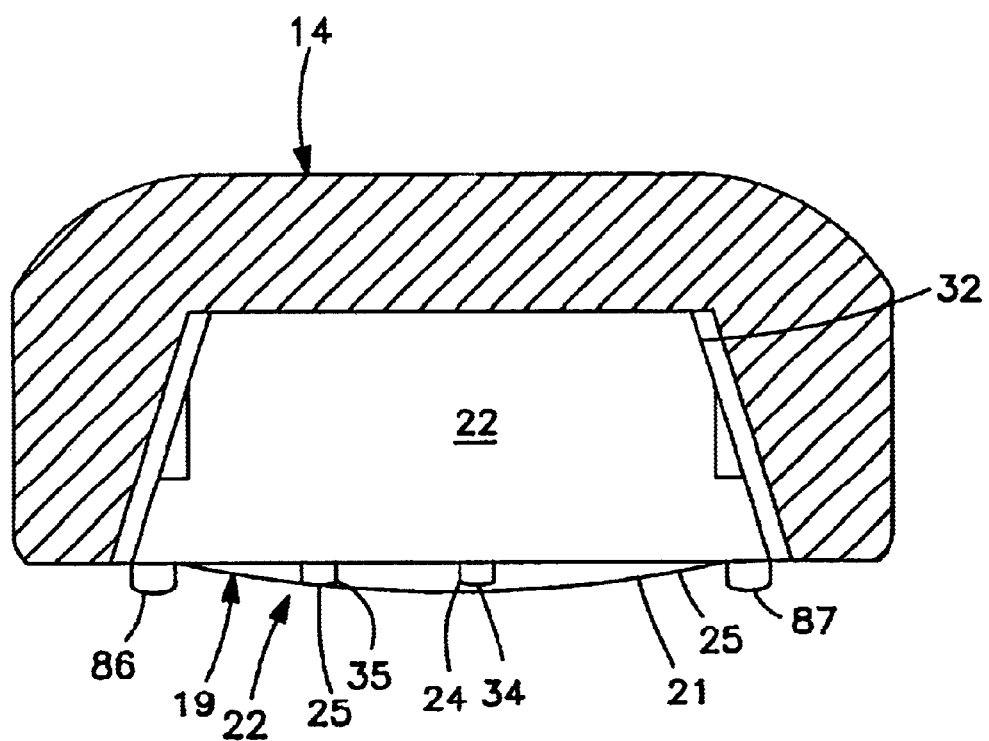
FIG. 10 of the drawings is a top plan view of the apparatus positioned on the forearm of a user.

Upon operative attachment, the first and second contacts of the power supply will be securely maintained in electrical contact with the corresponding first and second leads of the electrode assembly as a result of biasing means 19 (FIG. 10). The biasing means comprises a combination of first and second contacts 34, 35, respectively, of the power source having a length which extends at least slightly below the bottom of lower surface 83 (FIG. 4) of the electrode assembly when operatively engaged together, and, wherein at least a portion of the electrode assembly (where the first and second leads 24, 25, respectively, are located) comprises a material 21' which is capable of resistive deflection. Accordingly, upon operative engagement, the first and second contacts will push into the first and second leads to, in turn, cause the contacted portion of the leads and associated material 21' to deflect outward. While some deflection occurs, material 21' resists excessive deflection, and, in turn, actually maintains tight contact/continuity between the leads and corresponding contacts as a result of material 21' being operatively secured to first interface 22 by attachment pegs 86 and 87 (FIG. 10). These attachment pegs (or other attachment means) cause material 21' to counteract a significant portion of the deflection forces caused by the first and second contacts.

Iontophoretic drug delivery device 10 is operable by a user by first applying a medicament or a beneficial agent onto electrode pads 26, 28 of electrode assembly 12 by conventionally known means. Once applied, electrode assembly 12 is positioned on a portion of the body proximate the region which is to receive treatment. The electrode assembly is secured to the user by conventional means, such as adhesive 130 applied adjacent to electrode pads 26 and 28 (FIG. 4). Additional adhesion can also result from the hydrated electrode pads as well. Once secure, the user is ready to attach power source 14 to electrode assembly 12.

Specifically, power source 14 is oriented so that outer surface 82 of first interface 22 (FIG. 4) substantially abuts inner surface 66 of second interface 32 (FIG. 3). As the user directs the first and second interfaces together, the tapered configuration of outer surface 82 and the outwardly extending configuration of inner surface 66 guide the first and second interfaces together. Similarly, the elongated configuration of the inner and outer surfaces likewise cooperate to rotate the first interface relative to the second interface until the interfaces are secured in a desired alignment with each other.

As the user continues to press the two interfaces together, the outer surface and the inner surface continue to guide the structures into mating engagement. Once fully engaged, the electrical contacts of the power source abut electrical leads 24, 25 of electrode assembly 12 and force the electrode material 21' to deflect outward. The inherent elasticity of material 21', coupled with the securement of material 21' to first interface 22 by attachment pegs 86 and 87, maintains the material in a taught state throughout its deflection, to, in turn, maintain electrical leads 24, 25 biased in electrical abutment against electrical contacts 34, 35.

Once mated, retaining means 18 releasably secures the power source to the electrode assembly. Specifically, engagement regions 75 (FIG. 6) of tab 48 are biased into detents 46 (FIG. 4) positioned on outer surface 82 of electrode assembly 12. As a result, the first and second interfaces are precluded from undesired inadvertent detachment, for example, during treatment.

As the electrical contact is established between leads 24, 25 and contacts 34, 35, the apparatus administers the medicament/beneficial agent through the,tissue of the user. Once the treatment is completed, or it is otherwise desirable to remove the electrode assembly from engagement with the power source, the user merely pivots/presses tabs 48 about axis 73 until engagement region 75 releases from detent 46. At such time, the user can withdraw the power source, and, in turn, first interface 22 from mating engagement with second interface 32.

The foregoing description merely explains and illustrates the invention and the invention is not limited thereto except insofar as the appended claims are so limited, as those skilled in the art who have the disclosure before them will be able to make modifications without departing from the scope of the invention.

What is claimed is:

1. An iontophoretic drug delivery apparatus comprising:
   an electrode assembly having an upper surface, an outer surface, a first interface and two electrical leads;
   a power source having an inner surface, a second interface and two electrical contacts;
   means for facilitating mating engagement of one of the first interface and the second interface into the other of the first interface and second interface, wherein the mating means includes a tapering structure associated with the outer surface of the first interface, wherein the tapering structure is wider at the upper surface, from which it depends, and
   means for facilitating mating engagement wherein the mating means includes an outwardly expanding structure associated with the inner surface of the second interface, to, in turn, enable slidable mated engagement between the first and second interface.

2. The apparatus of claim 1 wherein the tapering structure and the outwardly expanding structure each comprise corresponding conical configurations.

3. The apparatus of claim 2 wherein the tapering structure comprises a non-uniform conical configuration.

4. The apparatus of claim 1 wherein the facilitating means comprises means for rotatively positioning at least one of the first interface and the second interface into a desired alignment with the other of the first interface and the second interface.

5. The apparatus of claim 4 wherein the rotative positioning means positions the first and second interfaces into at least two desired angular orientations.

6. The apparatus of claim 1 further comprising means for retaining the first and second interfaces in a desired mated orientation.

7. The apparatus of claim 6 wherein the retaining means comprises at least one detent associated with one of the first and second interfaces and at least one selectively engageable biased tab associated with the other of the first and second interfaces, whereupon the at least one biased tab lockably cooperates with an associated detent upon positioning of the first and second interfaces into the desired mated orientation.

8. The apparatus of claim 1 further including means for biasing the leads of the electrode assembly by the electrical contacts of the power supply upon mated engagement of the first and second interfaces.

9. The apparatus of claim 8 wherein the biasing means comprises:
   at least one of the two electrical contacts associated with the second interface having a length which extends below the bottom of the first interface when matingly engaged; and
   an elastically deformable material associated with at least one of the two electrical leads, such that, upon mated engagement of the first and second interfaces, the at least one electrical contact of the second interface deflects the elastically deformable material outwardly, to, in turn, result in secure electrical continuity between the at least one electrical contact and the at least one electrical lead.

10. The apparatus of claim 9 further including means for retaining the mated engagement of the first and second interface, to in turn, maintain the elastically deformable material in an elastically deformable orientation.

11. The apparatus of claim 10 wherein the retaining engagement means comprises a portion of the elastically deformable material being securely attached to the first interface.

12. The apparatus of claim 1 further including a seal member associated with at least one of the first and second interface, the seal member sealing the underside of the power source from undesired contamination.

13. An iontophoretic drug delivery apparatus comprising:
   an electrode assembly having a first interface and at least two electrical leads;
   a power source having a second interface and two electrical contacts, wherein the first and second interfaces are capable of operable mating engagement in at least two orientations;
   means for electrically connecting the two electrical leads with the electrical contacts in any of the at least two orientations.

14. The apparatus of claim 13 wherein the first and second orientations are achieved by rotating one of the electrode assembly and power source relative to the other about an axis, the electrical connecting means comprising the positioning of a first electrical lead of the electrode assembly about the axis of rotation and the positioning of one of the two electrical contacts of the power source about the axis of rotation.

15. The apparatus of claim 14 wherein:

the second electrical contact is spaced apart from the axis of rotation a predetermined distance, and, wherein, a second electrical lead is positioned a predetermined distance apart from the axis of rotation, and the second electrical lead is positioned so that the second electrical contact engages the second electrical lead in any of the at least two orientations.

16. The apparatus of claim 13 further including means for biasing the electrical leads of the electrode assembly with the electrical contacts of the power supply upon mated engagement of the first and second interfaces.

17. The apparatus of claim 16 wherein the biasing means comprises:

at least one of the two electrical contacts associated with the second interface having a length which extends below the bottom of the first interface when matingly engaged; and an elastically deformable material associated with at least one of the two electrical leads, such that, upon mated engagement of the first and second interfaces, the at least one electrical contact of the second interface deflects the elastically deformable material outwardly, to, in turn, result in secure electrical continuity between the at least one electrical contact and the at least one electrical lead.

* * * * *